United States Patent [19]
Hahn et al.

[11] Patent Number: 5,645,563
[45] Date of Patent: *Jul. 8, 1997

[54] CHILD-BIRTH ASSISTING SYSTEM

[75] Inventors: Soonkap Hahn, Poway; John Merritt, San Clemente, both of Calif.

[73] Assignee: Novatrix, Inc., San Clemente, Calif.

[*] Notice: The term of this patent shall not extend beyond the expiration date of Pat. No. 5,405,356.

[21] Appl. No.: 377,145

[22] Filed: Jan. 24, 1995

Related U.S. Application Data

[63] Continuation-in-part of Ser. No. 86,099, Jun. 30, 1993, Pat. No. 5,405,356.
[51] Int. Cl.⁶ .................................................. A61B 17/42
[52] U.S. Cl. .............................................. 606/202; 128/775
[58] Field of Search ................................. 606/119, 121, 606/201, 200; 128/775, 778

[56] References Cited

U.S. PATENT DOCUMENTS

| | | |
|---|---|---|
| Re. 31,158 | 2/1983 | Carter et al. . |
| 2,597,637 | 5/1952 | Heidenwolf . |
| 4,294,261 | 10/1981 | Baker et al. . |
| 4,321,929 | 3/1982 | Lemelson et al. . |
| 4,520,820 | 6/1985 | Kitchin et al. . |
| 4,531,516 | 7/1985 | Poole et al. . |
| 4,534,338 | 8/1985 | Crosbie et al. . |
| 4,548,198 | 10/1985 | Manes . |
| 4,736,731 | 4/1988 | Van Patten . |
| 4,873,986 | 10/1989 | Wallace . |
| 4,949,730 | 8/1990 | Cobben et al. . |
| 5,174,281 | 12/1992 | Lee . |
| 5,383,893 | 1/1995 | Daneshvar ........................ 606/202 |
| 5,405,356 | 4/1995 | Hahn et al. ....................... 606/202 |
| 5,464,420 | 11/1995 | Hori et al. ......................... 606/202 |

FOREIGN PATENT DOCUMENTS

| | | |
|---|---|---|
| 2198 | of 1989 | China . |
| 1800287 | 4/1970 | Germany . |

OTHER PUBLICATIONS

An Application of PVDF-film to Medical Transducers by Kenji Kobayashi and Tstutomu Yasada, *Ferroelectrics*, 1981, vol. 32, pp. 181–184.

*An Application of PVF₂ to Fetal Phonocardiographic Transducer* by F. Steenkeste and Moschetto.

Microphones with Rigidly Supported Piezopolymer Membranes by R. Lerch and G.M. Sessler *Journal of Acoustical Society of America*, 67(4), Apr. 1980, pp. 1379–1381.

Primary Examiner—Michael Powell Buiz
Assistant Examiner—William Lewis
Attorney, Agent, or Firm—Brown, Martn, Haller & McClain

[57] ABSTRACT

The childbirth-assisting device uses an automatically synchronized expandable pneumatic girdle to externally augment the secondary force of labor. The girdle through which the pressure is applied is fitted around the abdomen of the woman. An inflatable bladder within the girdle is inflated to create a downward pressure on the abdomen upon detection of a contraction. External pressure monitors which detect contractions may be attached directly to the girdle, and the girdle is configured to assure that the bladder is correctly positioned at all times. A member may be provided to prevent multiple uses of a girdle to assure the integrity of the girdle during use.

18 Claims, 5 Drawing Sheets

CHILD-BIRTH ASSISTING SYSTEM

This is a continuation-in-part of application Ser. No. 08/086,099, filed Jun. 30, 1993, now U.S. Pat. No. 5,405,356.

FIELD OF THE INVENTION

The invention generally relates to the field of labor assisting devices, and specifically to a device which simulates the secondary force of labor.

BACKGROUND OF THE INVENTION

A normal labor process is divided into three stages. Among these stages, the first and second stages are the crucial ones which are directly involved in the delivery of fetus. The first stage of labor begins with the onset of rhythmic uterine contraction and ends at the complete dilation of the cervix which is about 10 cm in diameter. The complete dilation of the cervix marks the beginning of the second stage of labor which ends immediately after the birth of the fetus. The third stage of labor extends from the birth of the baby to the complete expulsion of the placenta. The labor progress is driven by two types of labor forces. The primary force is produced by the involuntary contractions of uterine muscle. The secondary force is produced by the increase of intra-abdominal pressure through voluntary contractions of the abdominal muscles and diaphragm. These forces cause an increase of intrauterine pressure to provide a critical expulsion force on fetus.

As often seen in clinical practice, systemic analgesic drugs, epidural anesthesia and long duration of exhaustive labor all can lead to the weakening of secondary force, and sequentially to delayed labor duration or even dystocia (arrest of labor). Numerous clinical studies have correlated a prolonged labor duration and dystocia with many undesirable outcomes, such as higher rate of infant mortality, neonatal seizures and postpartum hemorrhage. To solve these serious problems, clinical instruments (forceps or vacuum suction) or cesarean section are often required to terminate labors. However, both instrumental delivery and cesarean section are far from trouble-free. While a cesarean section is basically safe, it remains a major surgical procedure. Patients who give birth by cesarean section are at much greater risk of childbirth-related illness or death than women who deliver vaginally. Also, the average cesarean birth has a length of hospital stay double that of a normal delivery and costs up to three times as much. Instrumental delivery also has limitations and may result in numerous complications including head and facial injuries to fetus. Therefore, it is in the best interest of both mother and fetus to prevent the incidence of prolonged duration of labor or dystocia.

One method of decreasing the incidence of prolonged labor is oxytocin infusion, which is commonly used in clinical practice to increase the primary labor force by directly inducing uterine contraction. Clinical evidence has demonstrated that oxytocin alone can only partially solve the problem of prolonged labor and dystocia associated with epidural anesthesia. However, a high incidence of cesarean section still occurs in patients receiving epidural anesthesia in spite of a high dosage of oxytocin infusion. Furthermore, high doses of oxytocin has been implicated in uterine tetanus and in some adverse neonatal outcomes, including fetal asphyxia.

Devices directed toward assisting in delivery are disclosed in the prior art. In the apparatus of Heidenwolf (U.S. Pat. No. 2,597,637, issued May 20, 1952), an inflatable bladder is held against the woman's upper abdomen by a wide belt. Extending from the bottom of the belt is a pair of straps which, in turn, attaches to straps surrounding the upper thighs. This structure holds the belt down to prevent slippage.

In the birth-assisting pneumatic cuff of Lee (U.S. Pat. No. 5,174,281, issued Dec. 29, 1992), an inflatable bladder fits over and around the woman's abdomen and is manually inflated and deflated in coordination with the patient's voluntary straining during the second stage of labor. This device applies pressure equally to the entire abdomen.

The Chinese patent of Fei Chao (Chinese Patent No. 2198, issued in 1989) teaches an abdominal girdle which has a generally triangular bladder (to match the rough contour of the uterus) which is placed over the patient's abdomen. The bladder is inflated manually in coordination with the woman's contractions to apply a downward pressure on the abdomen, assisting in forcing the fetus downward. While the girdle itself is very effective, the manual control of the inflation/deflation may not be easily accepted by physicians who may be reluctant to rely on a device which could be easily subject to human error with serious consequences.

Related prior art may be seen in the areas of anti-G pressure suits and in inflatable tourniquets and splits. Examples of pressure suits are taught by Crosbie et al. in U.S. Pat. No. 4,534,338, issued Aug. 13, 1985, and Van Patten, U.S. Pat. No. 4,736,731, issued Apr. 12, 1988. These suits inflate in response to changes in the rate of acceleration of an aircraft. Poole, et al. (U.S. Pat. No. 4,531,516, issued Jul. 30, 1985), Manes (U.S. Pat. No. 4,548,198, issued Oct. 22, 1985) and Kitchin et al. (U.S. Pat. No. 4,520,820, issued Jun. 4, 1985) teach inflatable devices for first aid applications. The latter two patents include disclosure of controllers for maintaining constant pressure, however none of these patents addresses synchronization of inflation/deflation as would be required for a labor- and delivery-assisting device.

BRIEF SUMMARY OF THE INVENTION

It is an advantage of the present invention to provide a device for assisting in delivery by simulating the secondary force of labor.

It is another advantage of the present invention to provide a childbirth-assisting device which is synchronized with uterine contractions.

Still another advantage of the present invention is to provide a means for preventing prolonged labor while avoiding cesarean section.

In an exemplary embodiment, the childbirth-assisting device uses an automatically synchronized expandable pneumatic girdle to externally augment the secondary force of labor. The pneumatic girdle with a generally triangular bladder (as taught by Fei Chao) is fitted around the abdomen of the woman and the girdle is inflated to create a downward pressure on the abdomen when a contraction occurs. The synchronization of the girdle's inflation and the contractions is provided by a microprocessor-based electronic controller which receives a signal from an intra-uterine monitor indicating a contraction and commands the girdle to inflate at a certain rate until a preset intra-uterine pressure is attained. Once the intra-uterinepressure reaches the pre-set pressure, the girdle pressure is maintained until the offset of the contraction is detected, at which time the girdle is deflated. The electronic controller, with programming utilizing rule-based methods, constantly monitors and initiates alarms for hazardous conditions including excessively long contraction periods, paired contractions, skewed contractions and other types of irregular contractions. The controller controls the girdle pressure according the stage of labor and distinguishes between actual and "false" contractions, which may be detected by the intrauterine monitor when the patient moves.

The childbirth assisting device can potentially be used in both the first stage and the second stage of labor. During the first stage of labor, the device can increase the abdominal pressure, aiding in the effacement of the cervix and hastening the descent of fetus and the cervical dilation process. During the second stage of labor, the device can provide a critical expulsion force for delivery of the fetus.

The childbirth assisting device can efficiently and safely prevent prolonged duration of labor and dystocia due to systemic analgesia, epidural anesthesia, or maternal exhaustion, which can lead to reduction of the cesarean section rate and rate of instrumental delivery. Since weakening of the secondary labor force is particularly common in patients receiving epidural anesthesia, the device can effectively prevent weakening of the secondary labor force under anesthesia, enabling a safer and less painful delivery.

By reinforcing the secondary labor force, the childbirth assisting device can further reduce the rate of cesarean section associated with dystocia and also lower the dosage of oxytocin. Functioning through different mechanisms, the device can be used to complement the benefits of oxytocin in clinical practice.

BRIEF DESCRIPTION OF THE DRAWINGS

Understanding of the present invention will be facilitated by consideration of the following detailed description of a preferred embodiment of the present invention, taken in conjunction with the accompanying drawings, in which like reference numerals refer to like parts and in which.

DETAILED DESCRIPTION OF A PREFERRED EMBODIMENT

Figure 1:
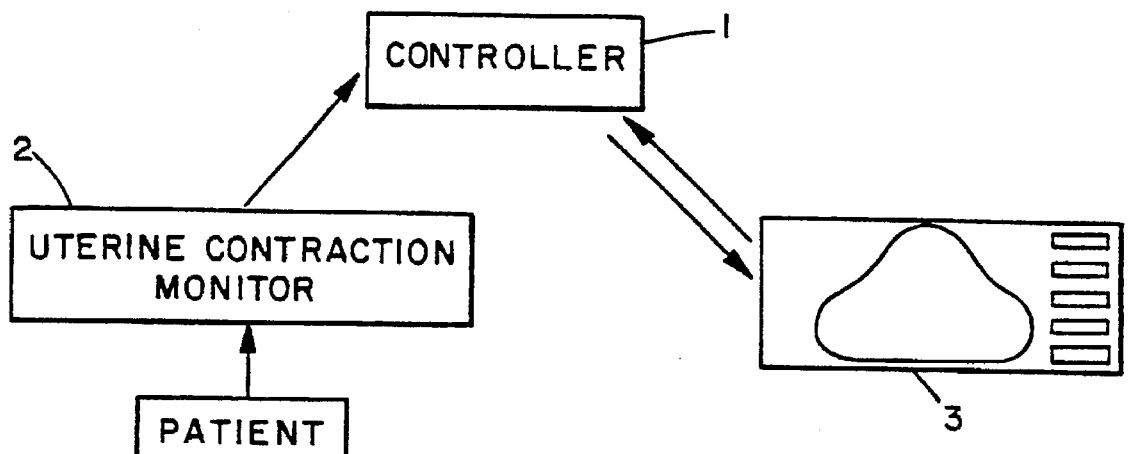
FIG. 1 is a block diagram of function of the childbirth assisting system of the present invention.

FIG. 1 is a block diagram of the childbirth assisting device including a patient and a uterine contraction monitor 2. A closed loop system uses patient response and rule-based decision making methods to achieve operator specified responses. The inventive device is a pneumatic closed loop system which is composed of an abdominal girdle 3 and a controller 1. The controller 1 possesses five main functions:

1. Receiving the uterine activity data from the uterine contraction monitor 2 and detecting the onset and offset of contractions.
2. Synchronizing the girdle pressure with the contraction, increasing the girdle pressure at the onset of contraction and decreasing it at the offset of contraction.
3. Adjusting the girdle pressure automatically to obtain the intrauterine pressure at a preset level.
4. Displaying information, including the girdle pressure.
5. Setting an alarm or alert system for abnormal situations.

The uterine contraction activity can be monitored either internally or externally. Internal pressure monitoring provides the most accurate assessment of uterine activity by allowing pressure changes in the uterus to be transmitted via a fluid-filled catheter to a strain gauge transducer. This produces quantitative readings of the duration, frequency, and amplitude of the uterine contraction, as well as the baseline tone of the uterus. An external tocodynamometry, which can be applied easily at any stage of labor, provides a non-invasive method of assessing uterine contractions. This yields a fairly reliable estimate of frequency of the contractions but a less accurate reading of the contraction intensity than an intrauterine catheter. The actual amplitude of the contraction cannot be measured by this method. In the preferred embodiment, the controller 1 receives the uterine activity data from an internal pressure monitor 2. The internal pressure monitor provides the accurate intrauterine activity data to the controller, which are necessary for improving the safety and efficiency of inventive device.

Figure 4:
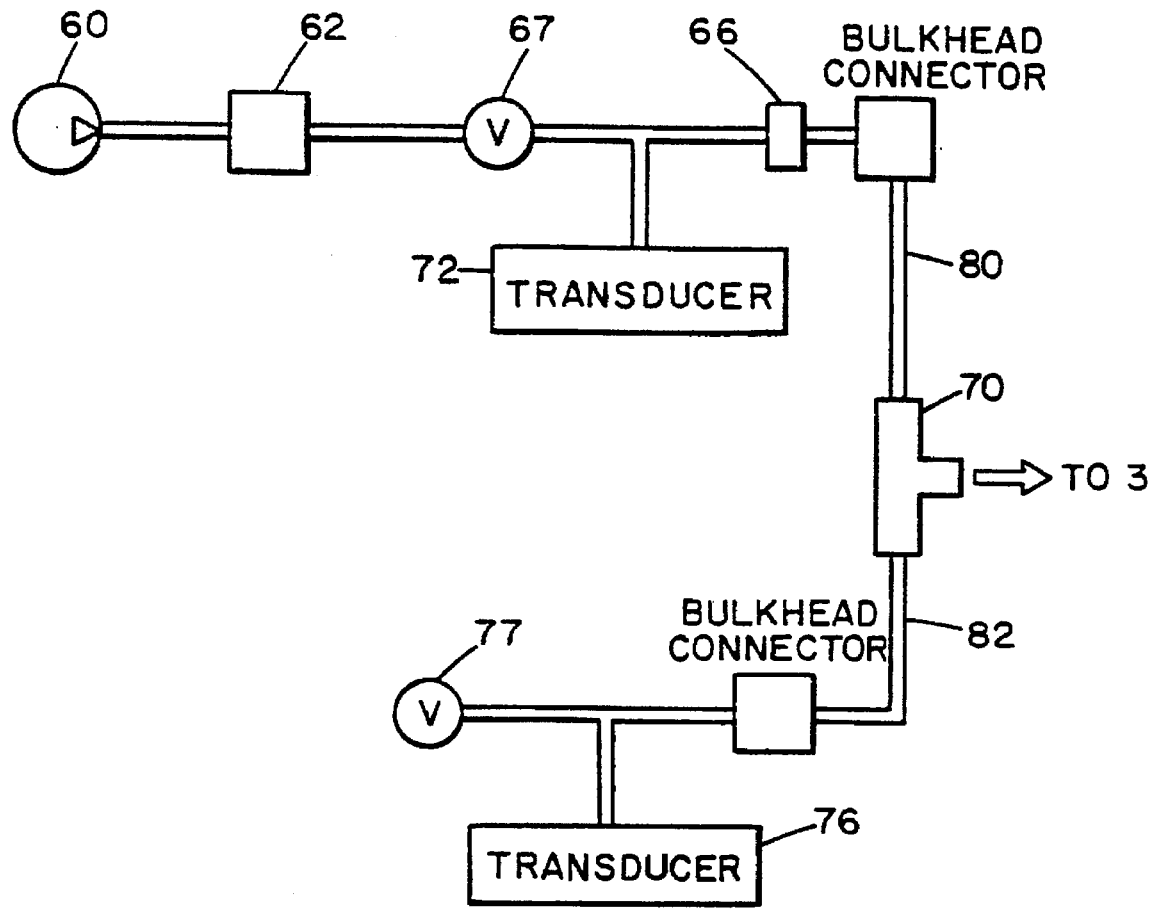
FIG. 4 is a block diagram of the pressure feedback loop of the prototype system.

Alternately, the inventive system may operate on an open loop principle which comprises a modification of functions 2 and 3 listed above. In the open loop system, application and release of girdle pressure need not rely on intrauterine pressure. Instead, application of pressure to the girdle will be triggered by detection of contraction pressure by the external toco sensor only, and only after a pre-determined threshold pressure is attained and held for a specified period of time. Once inflated, the girdle pressure is maintained for a fixed duration, e.g., 30 seconds, after which the release valve is automatically opened to deflate the girdle. The prototype embodiment of FIG. 4 is an open loop system.

Figure 2:
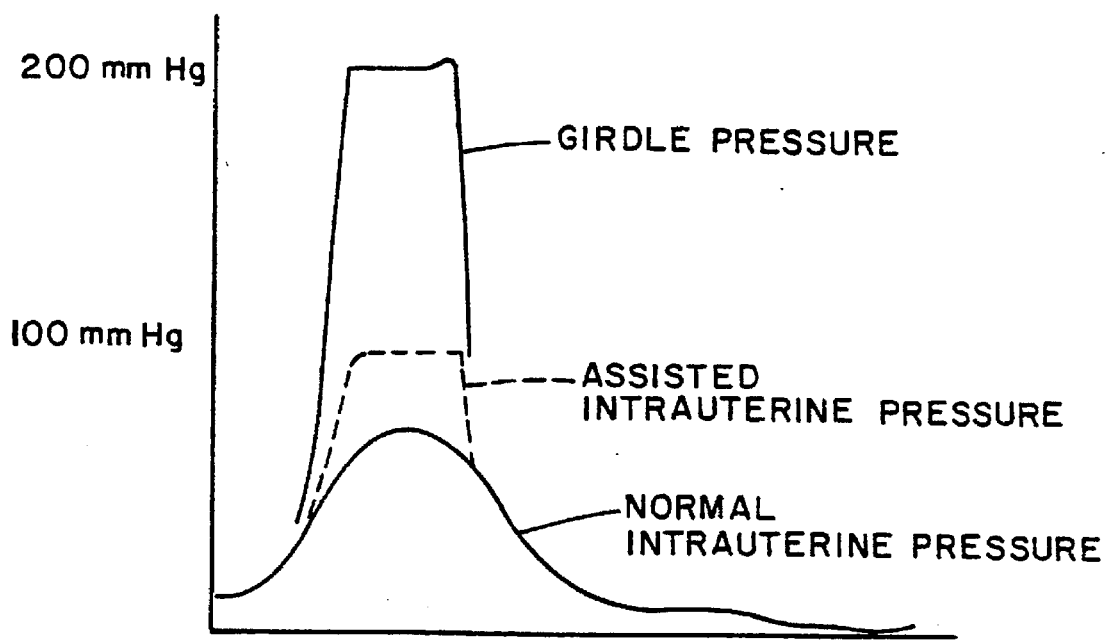
FIG. 2 is a plot of pressure versus contraction duration.

The normal uterine contraction curve is bell-shaped, as shown in FIG. 2, with the descending limb returning to the same basal level as preceded the ascending limb. At the beginning of the first stage of labor with cervical dilation up to 3 cm, an average increase in maximum uterine pressure above basal level is about 20–30 mmHg while at the active phase, with cervical dilation from 3 cm to 10 cm and the second stage of labor, it is in the range of 40–50 mmHg. Contraction frequency also increases from two to three per 10 minutes to four to five per 10 minutes at the end of labor. On slow rise of uterine pressure, the controller evaluates the uterine activity data and determines the onset of contraction. Once the controller 1 detects the onset of contraction, the girdle pressure will be increased. Determining the onset of contraction is somewhat arbitrary. This invention may not be recommended for use during the early first stage of labor including the early active phase (cervical dilation up to 6–7 cm). In the preferred embodiment, the onset of contraction is set at 15–20 mmHg above the basal level. At the onset of contraction, the girdle pressure is increased at the preset rate until the preset intrauterine pressure is obtained. Once the intrauterine pressure reaches the preset pressure, the girdle pressure will be maintained to obtain a constant intrauterine pressure. The offset of contraction can be detected when the girdle pressure increases sharply, as shown in FIG. 2. The girdle pressure will be released upon detection of the offset of contraction.

Figure 5:
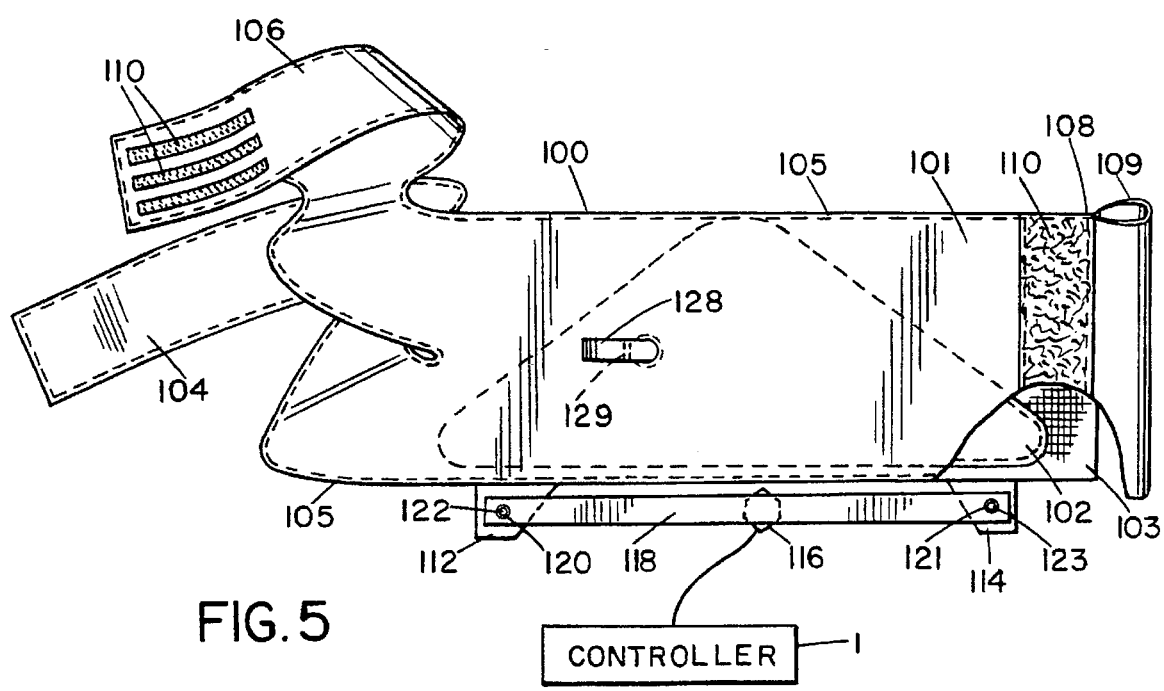
FIG. 5 is a diagrammatic front view, partially cut away, of a first embodiment of the girdle for use with the present invention.

The girdle 3, illustrated in detail in FIG. 5, is formed of two basic components: the belt 100 and the bladder 102. The design of the belt requires two considerations. The inner lining must be soft and comfortable to the mother while the outer lining must have high tensile strength so that it can be tightly secured around the mother to keep the bladder inflation pressure downward against the abdomen. The belt 100 may be formed from polyvinylchloride (PVC) or an elastomer-coated fabric, such as polyurethane-coated nylon. For the patient's comfort, the interior lining of the belt which comes in contact with the skin should be a soft fabric, such as the loop material of a hook-and-loop fastener, velour, woven fabric such as cotton or nylon, netting, or a combination of materials including a laminate. The choice of materials will depend on the integration of the bladder. For example, the belt could serve as the reinforced lining to the bladder, or it could be part of the bladder. An elastomer coating on outer layer of the belt may be added to prevent the fabric from stretching, or the outer surface may be non-stretch cotton fabric or surgical tape. In one version illustrated in FIG. 5, the belt is originally formed in two layers 101 and 103 so that the bladder 102 may be inserted between the layers. (Layer 101 represents the outer PVC layer and layer 103 represents the inner fabric-lined layer.) The layers may be sealed together after the bladder is inserted to firmly retain the bladder at a fixed position within the belt. The sealing welds 105 are indicated as dashed lines. Alternatively, the bladder 102 may be floating, sealed to only one of the two layers of the belt, or unattached to either layer and simply retained between the two layers once they have been sealed together. Selection of belt configuration may be made based upon pressure transfer efficiency, with the floating bladder version having demonstrated improved pressure transfer in prototypes of the invention. The choice of material of which the belt is made will depend upon whether the bladder is attached or floating.

Figure 6:
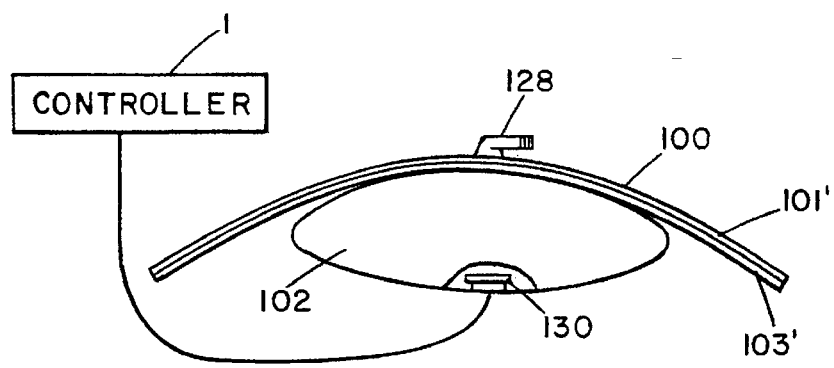
FIG. 6 is a side elevation of a second embodiment of the girdle.

In another embodiment shown in FIG. 6, the inner and outer layers 101' and 103' are sealed together without placing the bladder between the layers. The bladder 102 is held directly against the mother's abdomen, with the inward force of the belt providing means for maintaining the bladder in the proper location.

Belt tension is critical to the performance of the belt. In order to facilitate the best possible fit to the mother, the end of the belt may be split to form two separately adjustable straps 104 and 106, as shown in FIG. 5. Strips of Velcro®, or a similar hook-and-pile fastener 110, are sewn onto end 108 of the belt and onto the ends of straps 104 and 106. The split design allows for the closest possible fit. The fastener on straps 104 and 106 should have sufficient length to adjust the belt diameter as needed for a particular patient. In order to optimize the fit of the belt, finger loop 109 is formed in end 108 to provide an anchor for medical personnel to use while pulling the straps to the desired tension. The loop 109 may be formed by doubling over a small portion of the belt material, then welding it in place.

Due to the significant amount of monitoring equipment that is used during a delivery, it may become difficult to place certain sensors on the patient's abdomen in conjunction with the belt 100. One method for alleviating this is by providing tabs 112 and 114 at the lower edge of the belt 100 which permit attachment of the toco sensor directly to the belt, eliminating the need for an additional toco belt. The toco sensor 116, which monitors the contractions, is mounted on an elastic fabric 118 with eyelets 120, 121, adhesive strips, hook-and-pile fasteners or snaps at either end which attach to corresponding fasteners 122, 123 on tabs 112, 114. With a standardized length between the eyelets 120, 121, since the tabs 112, 114 are at a fixed distance (17.5" in the preferred embodiment), this provides a further advantage in that the toco sensor is always maintained at the same tension against the mother's abdomen.

The expandable bladder 102 may be formed from a thin reinforced polyurethane, polyvinyl chloride (PVC), silicone, or similar elastomeric membrane material. In the embodiment of FIG. 5, the bladder is sandwiched between and welded to the belt material so that the bladder cannot move within the belt. Inflation nipple 128 extends from bladder 102 through an opening in the belt 100.

Figure 10:
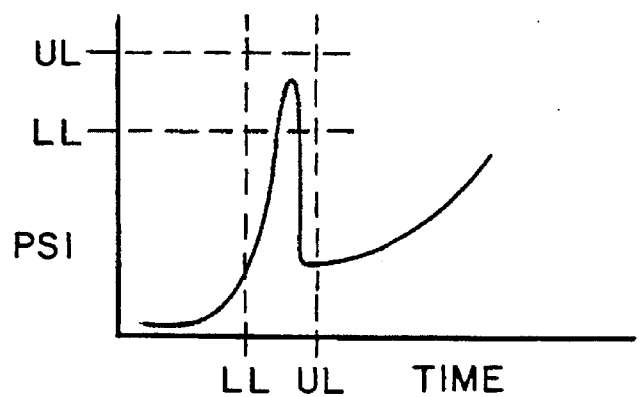
FIG. 10 is an exemplary plot of an indication of backpressure for assuring single use.

The material of which the preferred embodiments of the belt and bladder are made are selected to permit the girdle to be economically manufactured as a single-use, disposable item. For safety reasons, to assure that the girdle is not weakened or degraded by multiple uses, the inflation nipple 128 can include means for assuring that a girdle is used only once. The single use means can be a break seal/plug incorporated into the inflation nipple 128 which, once connected to the monitor and air supply hoses must be broken to remove it, preventing its reuse. Other means for assuring single uses of the girdle can be a peel away connector in the inflation nipple 128, a piezo film, or a rupture film built into the nipple 128. The rupture film 129 (shown diagrammatically as dashed lines in FIG. 5) spans the interior of the nipple 128 and works in cooperation with the controller 1. When the air supply hoses 24A and 24B are connected to the girdle (referring to FIG. 3), an initial burst of air can be provided to rupture the film 129. The sense valve 9 will detect a backpressure and the controller 1 will have stored data regarding a pre-set pressure threshold value at which rupture of the film should occur. If the threshold backpressure is not attained, this may be an indication that the film 129 was already ruptured in a previous use of the girdle. Software within the controller 1 will prevent any further use of the system until a new girdle is detected by way of the proper backpressure. An exemplary plot of detection of a seal by backpressure showing hypothetical upper and lower limits (UL and LL) for as thresholds for confirming correct backpressure and time to rupture is provided in FIG. 10.

A piezo film would function in a similar manner, with the film, itself, providing the signal indicative of the pressure being applied during the initial burst. Alternately, an electrically conductive strip could be built into the nipple 128 which can be detected by causing a change in resistance of electrical wiring built into the air tubing.

An alternate solution to the problem of a limited area on the mother's abdomen on which a number of different devices need to be place is to utilize the bladder 102 itself as part of the contraction sensor. This is favorable because the bladder membrane is sound sensitive and will conduct the acoustic waves for pick-up by a sensor 130 built into the bladder, as shown in FIG. 6.

Figure 7:
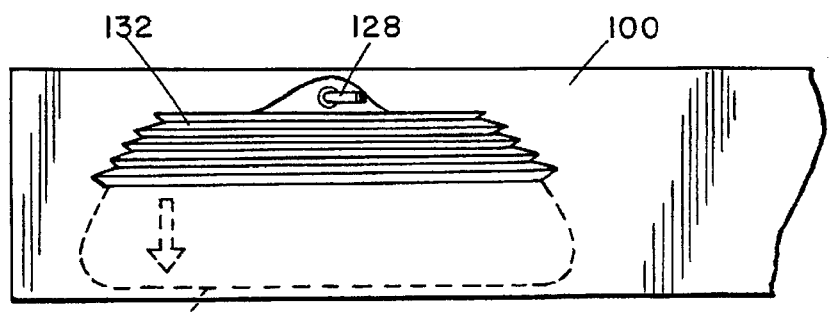
FIG. 7 is a diagrammatic front view of a third embodiment of the girdle.

A second alternate solution to working within the limited space is to form the bladder with fan-folds 132 or accordion pleats, as illustrated in FIG. 7. Here, when the bladder is deflated it covers only a small area of the abdomen. Upon inflation, the bladder expands within the belt into the area indicated by dashed lines 136 to apply pressure in the appropriate direction. A pocket within the belt controls the direction of expansion of the bladder to assure that the pressure is dispersed uniformly and in the proper direction. When the bladder is inflated, the readings from the toco sensor are not as critical, so expanding the bladder over the toco sensor is not a problem.

Figure 8:
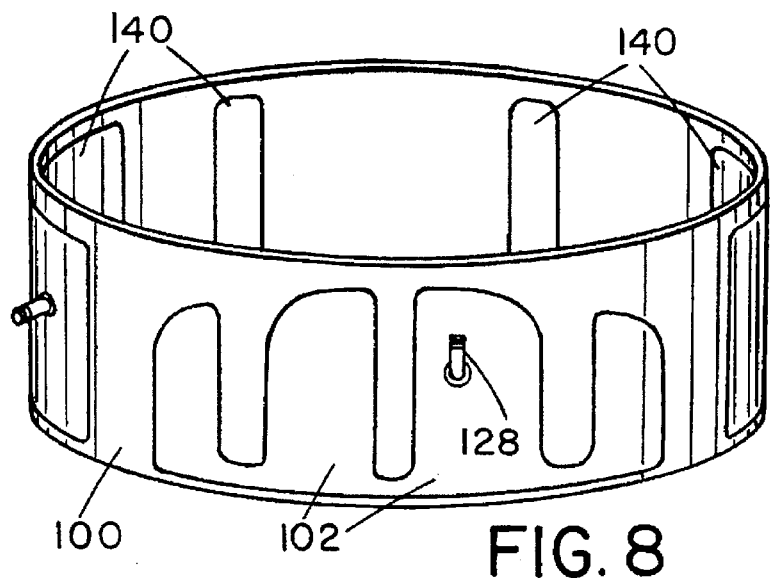
FIG. 8 is a perspective of a fourth embodiment of the girdle.

The girdle may also incorporate one or more separate bladders 140 which are controlled independently of the primary labor-assisting bladder 102 to regulate overall belt pressure and to add lumbar support. This embodiment is shown in FIG. 8. Note that the primary bladder 102 is shown in a slightly different configuration from the typical triangular shape. The shape of the primary bladder is not limited to a triangle, nor must the size be fixed. It can be varied as needed to apply the desired pressure appropriately. Secondary bladders 140 help reposition the patient during periods of discomfort. Inflation of bladders 140 can be coordinated with contractions to alleviate lower back pain associated with the contractions, or inflation can simply occur at fixed intervals to provide a massaging function. Bladders used for regulating belt tension can alleviate pressure from the epidural and spinal column, making belt application easier.

Figure 9:
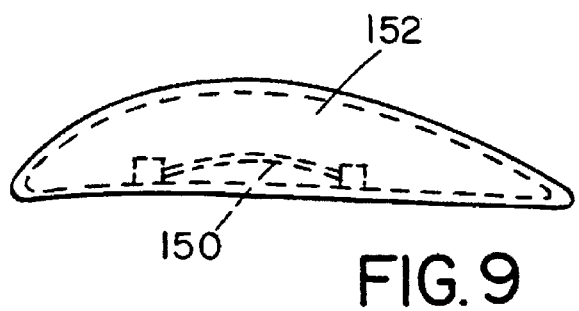
FIG. 9 is diagrammatic side elevation of an alternate embodiment of the bladder/sensor combination.

The sensor for detecting contraction and fetal heartbeat may be incorporated into the girdle as described above in the form of a toco sensor, or may utilize ultrasound, pressure sensitive ink or piezo film 150, which may be incorporated into the fabric of the belt or in the bladder 152 (see FIG. 9), or air/fluid displacement. The piezo film 150 may be polyvinylidene fluoride (PVDF), which transducers are known in the art. A representative discussion of such transducers for fetal heart sound detectors and uterine contraction monitors is provided in the article entitled "An Application of $PVF_2$ to Fetal Phonocardiographic Transducers", F. Steenkeste, et al., by F. Steenkeste and Moschetto. Three approaches for placement of the sensor(s) are: multiple small pockets located below the main bladder, a Velcro®-backed sensor that can attach to a loop lining on or around the main bladder, or a sensor sealed inside the main bladder, such as shown in FIG. 6. Multiple sensors may be used in series for greater reliability. Air pockets and bladders are ideal for housing small sensor because they can accurately and consistently apply the force necessary for reliable signal response, and they provide the direct capability to synchronize operations with the main bladder.

Figure 3:
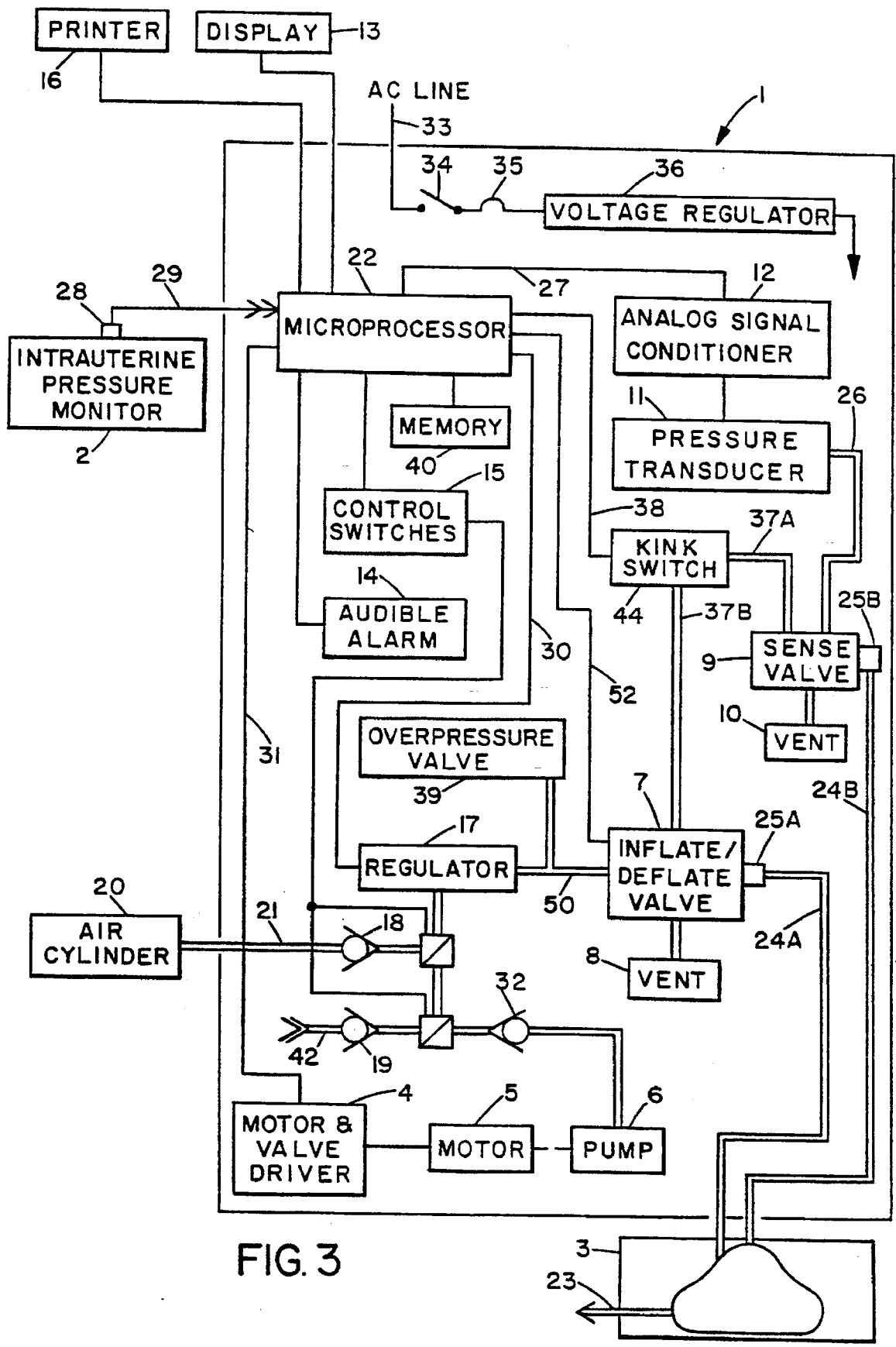
FIG. 3 is a block diagram of the components of the invention.

FIG. 3 is a block diagram of automatic labor assisting device, showing the details of the controller 1 and the girdle 3 according to the present invention. Within controller 1, a pressure sensing means, including pressure transducer 11 and analog signal conditioner 12, produces a signal which is fed into the microprocessor 22. The signal is quantized in a 12 bit analog-to-digital converter within the microprocessor 22. A display means, which includes a memory and signal processing circuitry within the microprocessor 22 and display 13, produces a pressure display of the girdle's internal pressure. A memory 40 within the controller provides storage for control parameters and a library of diagnostic information, which is described below in more detail. An inflatable girdle 3 is shown connected via tubing 24A and 24B to the controller 1 at coupling 25A and 25B. Coupling 25B is connected via valve 9 and pressure line 26 to pressure transducer 11. A signal representing the pressure measured by the pressure transducer 11 and analog signal conditioner 12 is applied via electrical line 27 to microprocessor 22. Two of the control switches 15 are used to apply a signal to microprocessor 22 to set a target intrauterine pressure and a maximum girdle pressure. A signal representing intrauterine pressure is applied to microprocessor 22 via connector 28 and electrical line 29.

Microprocessor 22 is programmed to calculate the girdle pressure adjustment proportional to the magnitude of the difference between the intrauterine pressure and the selected target pressure, and produces an output signal on line 30 which indicates the girdle pressure adjustment. A select switch in control switch 15 determines if an external air line via air line 42, an internal replaceable air bottle via air line 21, or an internal motor 5 and pump 6 are to be used to inflate the girdle. Note that all three air paths are isolated from each other via check valves 18, 19 and 32. The motor 5 is turned on and off by the microprocessor 22 via line 31 to a motor and valve driver circuit 4. The pressure to the girdle 3 is controlled by the regulator 17. Valve 7 vents the pressure in girdle 3 via vent 8 for a time determined by microprocessor 22 through line 52.

Power is applied to controller 1 through line 33 via switch 34 and circuit breaker 35. A voltage regulator 36 provides a 5 volt regulated voltage which is used to power the portion of the digital circuit requiring a positive 5 volts. The 12-volt voltage output is also provided for portions of the circuitry such as the valves, pumps and pressure transducer which require 12-volt power supply. Differential pressure switches 44 are connected between lines 37A and 38B. If any obstruction occurs between lines 37A and 37B, switches 44 apply a signal to microprocessor 22 through line 38 to sound an alarm.

The microprocessor 22 utilizes the information and the signals applied to it to control the girdle 3 and to provide information output. Signals applied from microprocessor 22 to the displays 13 and printer 16 include:

Target intrauterine pressure

Maximum girdle pressure

Current intrauterine pressure

Uterine pressure due to primary force

Current girdle pressure

Diagnostic information for doctor

Alarm for whether there is an obstruction (kink).

The microprocessor 22 compares the input signal received from the intrauterine monitor and the girdle pressure sensors against criteria which are stored in the memory 40. These criteria include the various pressure settings, as well as means for identifying the presence of abnormal contractions which may require modification of the operating parameters of the controller or may require removal of the girdle.

Signals are generated to sound alarm 14 whenever alarm conditions are met. The alarm may be silenced if desired via one of the control switches or by pressing an emergency stop button which will deactivate the controller and deflate the girdle. Sense valve 9 is connected between girdle 3 and pressure transducer 11. The sense valve 9 connects the pressure transducer 11 to atmosphere through vent 10 during the girdle start-up sequence in order to correct the pressure transducer zero offset. Overpressure valve 39 is connected to the line 50 between regulator 17 and inflate-deflate valve 7. This is a manually adjustable valve which limits the maximum pressure delivered to the girdle, in the event that all the safeguards in the air regulation line systems fail. In addition, safety valve 23 is designed into the girdle 3 to deflate the girdle in case of extreme overpressure which would endanger the fetus.

A prototype of the controller was designed with two feedback control loops. The first loop monitored and evaluated the activity of the uterine contraction. Intrauterine pressure was detected by a strain gauge operated with a bending beam mechanism. The output signal of the strain gauge ranged from 1 V at zero pressure to 5 V at 105 g of force. The signal generated by the strain gauge was digitized and transferred to the built-in microprocessor. The programming within the microprocessor caused the second feedback loop to be initiated once the intensity of the contraction reached a certain point (20% of full scale) and stayed over that point for 5 seconds. Using this criteria, a false signal generated by non-contraction processes such as physical movement by the patient could be filtered out.

The second feedback control loop, shown in FIG. 4, controlled the inflation and deflation of the girdle 3 using an air compressor 60. This loop is a slight modification of the system of FIG. 3. The girdle is connected to the air compressor 60 (Gast Manufacturing Corp. diaphragm compressor, 50 PSI maximum with 15 cubic inches per second air flow) through air line 80 with air valve 67 controlling the rate of inflation of the girdle 3. The girdle 3 may be deflated through air line 82 by opening air valve 77 and venting the girdle to atmospheric pressure. Each line is connected with its own transducer 72 or 76, each with an output of 1 V per 100 mmHg (Sensym, output range of 1 to 15 volts with a base voltage of 1 volt at 0 mmHg). Transducer 76, attached to air line 82, reads the air pressure coming into the girdle from the air compressor. When the onset of contraction is detected and meets the true contraction criteria, air passes through air line 80 until the internal girdle pressure reaches the target belt pressure established by the operator. When the girdle pressure reaches its target, air valve 72 switches off to block the air flow into the girdle.

If the girdle pressure drops, transducer 76 detects the drop, and air valve 67 is activated to re-pressurize the girdle to target pressure. As a safety mechanism, valve 77 opens 30 seconds after initiation of the inflation process to deflate the girdle.

To detect the occurrence of tube kinking, the microprocessor sets a minimum pressure increase of 10 mmHg for 5 seconds. Any rates below this are treated as tube kinking, triggering immediate deflation of the girdle and activating an audible alarm for 5 seconds or longer. If this safety device fails, an emergency stop button is provided. The emergency stop button opens valve 77 and closes valve 67 for emergency deflation.

Displaying various forms of outputs is an important function of the controller 1. The girdle pressure and the patient information are displayed on the screen.

To detect hazardous conditions or unexpected patient responses, numerous alert and alarm criteria may be optionally implemented within the device control software:

1. Setting a maximum duration at the target intrauterine pressure during the contraction: A normal contraction may last about 60–90 seconds. However, abnormal contractions such as polysystole, skewed contractions and tachysystole may show a longer contraction period due to a slow return to a baseline. This may result in applying the high pressure onto the abdomen over an extended period. To avoid this problem, the maximum duration at the target intrauterine pressure during the contraction will be established at 20–60 seconds. In the prototype, the limit was set at 30 seconds.
2. Setting an interval between two cycles of girdle pressure increase: Contraction frequency increases from two to three per 10 minutes to four to five per 10 minutes at the end of labor. Abnormal contractions such as paired contractions show much a shorter interval between two contractions. The use of the labor assisting device in this case may result in applying an excessive force to the abdomen in a short time period. This problem will be solved by setting a minimum interval between two cycles of girdle pressure increase. The minimum interval will be set at 1.5–5 minutes, with the prototype set at 1.5 minutes.
3. Setting the target intrauterine pressures at different stages of labor: In normal labor, an average increase in maximum uterine pressure above basal level begins with about 20–30 mmHg at the early first stage of labor and becomes 40–50 mmHg at the active phase and the second stage of labor. This force is mainly produced by the primary and involuntary force. In addition to the primary force, the use of the inventive device will increase the intrauterine pressure further by providing the secondary force. To enhance the safety of the device, the target intrauterine pressures are assessed during various phases of labor. For example, the target intrauterine pressure during the stage of labor with cervical dilation from 3 cm to 8 cm is set at 40–60 mmHg above the baseline while during the active phase with cervical dilation from 8 cm to 10 cm at 60–80 mmHg and the second stage of labor at 80–160 mmHg. The decision of whether the stage of labor is early or active should be made by a physician. Obstetricians also set up the appropriate target intrauterine pressure depending on clinical situations. Any uncontrollable intrauterine pressure increase above the target pressure (15 mmHg higher than the target) will trigger the alarm system and rapidly deflate the girdle.
4. Setting a limit of the girdle pressure at each target intrauterine pressure: This mechanism also prevents any extra force on the abdomen which may result from malfunctions of the device. For example, the limit of the girdle pressure will be set at 150 mmHg during the stage of labor with cervical dilation from 3 cm to 8 cm when the target intrauterine pressure is 40–60 mmHg. The limit will be set at 250 mmHg during the active phase of labor with cervical dilation from 8 cm to 10 cm when the target intrauterine pressure is 60–80 mmHg. The limit will be set at 350 mmHg during the second stage of labor. The girdle pressure above these limits triggers the alarm system and rapidly deflates the girdle. The girdle may also be implemented with its own safety valve which be blown if the pressure exceeds 350 mmHg. In the prototype, the safety valve was implemented by setting the maximum pressure of 350 mmHg in the controller software and by an inline air regulator 66 (in FIG. 4). If the girdle pressure exceeded 350 mmHg, valve 77 opened to deflate the girdle.
5. Filtering the false contractions: The movement of patient sometimes generates the sudden rise of intrauterine pressure. This can be filtered by evaluating the rate of intrauterine pressure increase, defined as a derivative, $dP/dt$, where P=intrauterine pressure and t=time, and comparing with a normal range of the rate. Any contractions with the rate of intrauterine pressure higher than the normal range will be treated as false contractions and will not trigger the inflation of the girdle.

In the prototype, a fault signal generated by non-contraction processes is filtered by setting a 5 second delay rule, i.e., a true contraction occurs if the intensity of the signal remains at 20% of full scale for 5 second.

For the safe use of the childbirth assisting device, several abnormal clinical situations have been considered. The criteria for each of these situations is stored within a library in the controller's memory 40 and the contraction data is compared against these criteria to determine whether the abnormal condition is present. If so, an alarm condition is initiated and an output is provided to indicate the presence of the abnormal condition. The following situations are included in the library of abnormal conditions:

1. Hypotonia/Hypocontractility:
   When contractions are less than 25 to 30 mmHg at their peak, or recur less frequently than every five minutes in the active phase of labor and last less than 45 seconds, hypocontractility is present, even if it is accompanied by progress in labor. The decreased uterine activity may be due to the abnormal contraction, hypotonia, or the artifact from the presence of air in the internal monitoring system. In both cases, the use of the device may not cause safety problems. However, since the device will not allow the girdle pressure to exceed the safety limit, the alarm system will be on before the target intrauterine pressure is obtained. The correction should be made upon a proper diagnosis of the above problems. The presence of air in the internal monitoring system can be corrected easily and device can be restarted.

2. Polysystole:

Polysystole is a common abnormal uterine waveform that is characterized by a single contraction with two or more peaks. It is also described as two or more contractions in juxtaposition without full return to the baseline between each. This could be determined by software and if the situation meets the alarm criteria set in the above section, the girdle should deflate and a physician should be informed.

3. Discoordinate uterine activity:

The constancy of the intervals between uterine contractions determines the degree of coordination or rhythm of uterine activity. When a marked variation occurs from contraction to contraction, the resultant pattern is termed "discoordinate labor". Because contractions may be generated from alternate uterine cornua as well as from other sites, frequent low intensity contractions are a typical finding. Since the controller sets up a threshold to evaluate the onset of contraction, some of the low-intensity contractions below this threshold may not trigger the girdle pressure to increase. This will be similar situation of hypotonia. In this case, the use of the device may not cause any safety problem. Other discoordinate labor, Uterine hypertonus, may result from the constantly contracting state of some area in the myometrium. Extreme degree of this phenomenon is uterine fibrillation. In this case, the use of the device should be avoided.

4. Skewed contractions:

A skewed contraction is characterized by a prolongation of the descending limb (relaxation phase) of the uterine contraction and is often seen in a mixed pattern with polysystole. The use of the inventive device implemented with a maximum duration at the target intrauterine pressure will not cause any problem.

5. Paired contractions:

Paired contractions are a form of increased uterine contraction frequently characterized by one uterine contraction in close temporal relationship to a second uterine contraction, with the waveform returning to baseline between the two contractions. Usually, the second contraction is smaller in amplitude. Since the device sets the minimum interval between two cycles of girdle pressure increase, its use under this condition will not cause any safety problem.

6. Tachysystole:

Tachysystole is defined as increased uterine contraction frequency. Because of the inevitable accompanying diminished or absent resting interval, decreased fetal oxygenation has been associated more often with this form of uterine hyperactivity than with increased intensity or duration of the uterine contraction. However, increased uterine activity of any type does not infer fetal stress or distress. Increased uterine activity may well be tolerated by some fetuses, whereas others may demonstrate stress even with uterine activity of a low intensity. As long as the fetus does not show distress, the use of the inventive device will not cause any problem. The software in device will diagnose the situation. However, a physician should make a final decision.

7. Tachysystole with progressive hypertonia:

Progressive hypertonia, usually associated with tachysystole, is a form of uterine dysfunction. It represents incomplete relaxation between frequently occurring contractions. The software in the inventive device will diagnose the situation. However, a physician should make a final decision about continued use of the device.

8. Tachysystole with progression to tetany:

Progressive uterine hypertonus, characterized as a rising baseline tone, is often accompanied by tachysystole. During the relaxation phase, the uterine tone does not completely return to the prior resting phase level before the next contraction begins. This may progress to tetany. The software in the inventive device will diagnose the situation. The use of the device should be decided by a physician under this circumstance.

9. Peaked contractions:

A contraction pattern of high intensity and frequency, with a peaked contour, has been associated with preeclampsia and eclampsia. The software in the labor assisting device will diagnose the situation. The use of the device should be decided by a physician under this circumstance.

10. Hypersystole:

The amplitude of intensity is the pressure difference (in mmHg) between the peak of the uterine contraction and the uterine tone preceding the contraction. Hypersystole is defined as greater than 60 mmHg maximum pressure. Contractions of greater than 60 mmHg are seen with pharmacologically overstimulated or spontaneous abnormal labor. If there is enough uterine pressure, the use of the device is not necessary. A physician will make a decision on continuing the use of the device.

The childbirth assisting device of the present invention effectively prevents prolonged duration of labor and dystocia due to systemic analgesia, epidural anesthesia, or maternal exhaustion, leading to reduction of the cesarean section rate and rate of instrumental delivery. Since weakening of the secondary labor force is particularly common in patients receiving epidural anesthesia, the device can effectively prevent weakening of the secondary labor force under anesthesia, enabling a safer and less painful delivery. The inventive device includes means for analyzing the contraction curve and period in order to identify the presence of abnormal conditions, providing further safety benefits.

By reinforcing the secondary labor force, the childbirth assisting device can further reduce the rate of cesarean section associated with dystocia and also lower the dosage of oxytocin. Functioning through different mechanisms, the device can be used to complement the benefits of oxytocin in clinical practice.

It will be evident that there are additional embodiments and applications which are not disclosed in the detailed description but which clearly fall within the scope and spirit of the present invention. The specification is, therefore, not intended to be limiting, and the scope of the invention is to be limited only by the following claims.

We claim:

1. An improved girdle for use in a system for assisting in childbirth, the system comprising a girdle having at least one inflatable bladder adapted to be positioned over a patient's abdomen for applying pressure to the abdomen, a contraction monitor for generating an electrical signal indicative of the patient's contractions, an automatic controller means in electrical communication with said contraction monitor for controlling the inflation and deflation of said at least one inflatable bladder in response to said electrical signal wherein the pressure is increased to a target intrauterine pressure at the onset of a contraction and decreased after the contraction is over, said automatic controller means having means for controlling air from an air source for inflating said girdle, and tubing having a first end attached to said girdle and a second end attached to said automatic controller means for conducting air between said girdle and said automatic controller means, the improved girdle comprising:

a belt having a first end, a second end, an upper edge, a lower edge, an inner layer and an outer layer, said inner layer having a soft contact surface for placement against the patient's abdomen, said outer layer being a non-expandable material, wherein said inner and outer layers are sealed together at at least said first and second ends and said upper and lower edges;

fastening means disposed at each of said first and second ends for releasably fastening said first end to said second end so that said belt fits closely around the patient's abdomen; and an inflatable bladder held by said belt at a position of said belt corresponding to the patient's abdomen so that said inflatable bladder is immovable, said inflatable bladder having an inlet means for connecting to said first end of said tubing for admitting air into said bladder.

2. An improved girdle as in claim 1 wherein said second end of said belt is split to form two separately adjustable belt sections.

3. An improved girdle as in claim 1 further comprising a finger loop formed in said first end of said belt.

4. An improved girdle as in claim 1 wherein inner layer comprises a fabric.

5. An improved girdle as in claim 1 wherein said bladder is sandwiched between said inner and outer layers of said belt.

6. An improved girdle as in claim 5 wherein said bladder is attached to at least one of said inner and outer layers.

7. An improved girdle as in claim 1 wherein said bladder is retained between said inner layer and the patient's abdomen.

8. An improved girdle as in claim 1 wherein said inlet means has a rupture membrane for providing a backpressure to a pre-determined level upon introduction of air.

9. An improved girdle as in claim 1 further comprising a pair of tabs extending from said lower edge of said belt and having second fastening means for attachment of the contraction monitor when the contraction monitor is a toco sensor mounted on an elastic band.

10. An improved girdle as in claim 1 further comprising at least one second inflatable bladder disposed within said belt at a position of said belt corresponding to a lumbar region of the patient.

11. An improved girdle as in claim 10 further comprising a second controller means for independently controlling inflation of said at least one second inflatable bladder and a second tubing interconnecting said at least one second inflatable bladder and said second controller means.

12. An improved girdle as in claim 1 wherein the contraction monitor is disposed within said bladder.

13. An improved girdle as in claim 12 wherein the contraction monitor is a piezo film.

14. An improved girdle as in claim 1 wherein said inflatable bladder has a plurality of pleats therein.

15. An improved girdle as in claim 1 wherein said inner and outer layers of said belt are welded together.

16. A girdle for use in conjunction with a controller for regulating air pressure in response to detection of an electrical signal indicative of a contraction during childbirth, the girdle comprising:

a belt having a first end, a second end, an upper edge, a lower edge, an inner layer and an outer layer, said inner layer having a soft contact surface for placement against a patient's abdomen, said outer layer being a non-expandable material, wherein said inner and outer layers are sealed together at at least said first and second ends and said upper and lower edges;

fastening means disposed at each of said first and second ends for releasably fastening said first end to said second end so that said belt fits closely around the patient's abdomen;

an inflatable bladder held by said belt at a position of said belt corresponding to the patient's abdomen so that said inflatable bladder is immovable, said inflatable bladder having an inlet means for connecting to said first end of a tubing connected to said controller for admitting air into said bladder; and a contraction monitor attached to said bladder and electrically connected to the controller for detecting uterine contractions and generating the electrical signal to which the controller responds.

17. A girdle as in claim 16 wherein said contraction monitor is a piezo film.

18. A girdle as in claim 16 further comprising means disposed within said inlet means for preventing reuse of the girdle.

* * * * *